United States Patent [19]

Heller

[11] 4,220,708
[45] Sep. 2, 1980

[54] PHOTOCHROMIC COMPOUNDS

[76] Inventor: Harold G. Heller, 11 Erw Goch, Waun Fawr, Aberystwyth, Wales

[21] Appl. No.: 846,148

[22] Filed: Oct. 27, 1977

Related U.S. Application Data

[63] Continuation-in-part of Ser. No. 719,254, Aug. 31, 1976, abandoned, which is a continuation-in-part of Ser. No. 599,975, Jul. 29, 1975, abandoned.

[30] Foreign Application Priority Data

Jul. 22, 1977 [GB] United Kingdom ............... 30894/77

[51] Int. Cl.$^2$ ..................... G03C 1/733; C07D 405/06
[52] U.S. Cl. .......................... 430/336; 260/326.5 SM; 260/326.5 D; 260/326.8; 260/326.55 A; 430/19; 430/339; 542/441; 542/442; 549/58; 549/60
[58] Field of Search ............................... 542/441, 442; 260/326.5 SM, 326.5 D, 332.2 H, 326.8, 330.5, 332, 326.55 A; 96/90 PC

[56] References Cited

U.S. PATENT DOCUMENTS 3,660,385  5/1972  Albrecht ............................... 542/441

FOREIGN PATENT DOCUMENTS 47-42267  10/1972  Japan .

OTHER PUBLICATIONS

Deohra et al, Chem. Abst. 62(1965), #7714(d).

*Primary Examiner*—Arthur P. Demers
*Attorney, Agent, or Firm*—Fleit & Jacobson

[57] ABSTRACT

Photochromic compounds are disclosed which are 3-furyl or 3-thienyl alkylidene succinic anhydrides or the corresponding succinimides. The compounds undergo reversible photocyclization on exposure to U.V. light in high yield and their cyclic forms are deeply colored making them suitable for a wide range of recording and display devices.

25 Claims, No Drawings

PHOTOCHROMIC COMPOUNDS

CROSS-REFERENCE TO RELATED APPLICATIONS

This application is a continuation-in-part of Ser. No. 719,254, filed Aug. 31, 1976, now abandoned, which is in turn a continuation-in-part of Ser. No. 599,975, filed July 29, 1975, now abandoned.

FIELD OF THE INVENTION

This invention relates to compounds exhibiting photochromism and useful applications of compounds having this property.

DESCRIPTION OF THE PRIOR ART

Photochromism can be defined as the phenomenon of a material to reversibly change its visible absorption spectrum on exposure to activating radiation and to revert to its original absorption spectrum on removal of the activating radiation or on substituting radiation of a different wavelength.

Organic photochromic compounds have been known for over a hundred years but they excited little commercial interest until the 1950's. In 1955 Y. Hirschberg (J.A.C.S. volume 78, page 2304–2312) investigated three photochromic spiropyrans and one bianthrone derivative which produced coloured forms on exposure to U.V. light and returned to their colourless state on exposure to visible light. Hirschberg measured the rate of formation of the coloured species and vice-versa in various media and concluded that none of the tested compounds would be suitable for the purpose he had in mind, namely data storage, because the rate of colour formation and the rate of bleaching were insufficiently rapid. A further problem encountered by Hirschberg and many subsequent investigators is that the coloured forms tend to be unstable at temperatures approaching normal ambient so that for many compounds the photochromic phenomenon can only be satisfactorily observed at temperatures in the region of $-60°$ C. or below. This obviously makes them unsuitable for practical use in commercial applications. In the search for commercially suitable photochromic compounds, one class of compounds which has been investigated by various workers are derivatives of bismethylene succinic anhydride, which are commonly referred to in the art as "fulgides". These were first described by Stobbe (Chem.Ber. 1904, 37 2236) who discovered a general procedure for their preparation which is still a commonly used process.

Santiago and Becker (J.A.C.S. 1968 90 page 2654) suggested that the primary process by which fulgides form coloured species is a photocyclisation but recognised that competing reactions occurred in the compounds tested. Specific fulgides and related compounds have also been prepared by El-Assal and Shehab (J.Chem.Soc. 1963 pages 3478–82), Brunow et al (Acta.Chem.Scand. 22, 1968, pages 590–5) and by Heller in British Pat. No. 1,271,655, but the fulgides described by these workers all show comparatively poor photochromic properties and exhibit irreversible side reactions, commonly known as fatigue, and poor thermal stability. Fatigue products adversely affect the photochromic properties and the properties deteriorate progressively with every colour/erase cycle.

In my co-pending patent application Ser. No. 801,915, filed May 31, 1977, now U.S. Pat. No. 4,145,536 there is described a series of photochromic compounds having the following general formula:

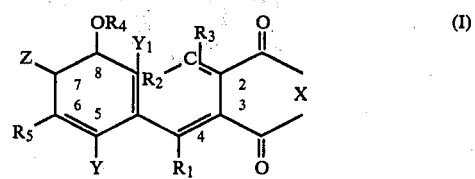

wherein X represent oxygen or $NR_6$, $R_6$ being hydrogen alkyl, aryl or aralkyl.

$R_1$ represents hydrogen, alkyl, aryl or aralkyl,

Y and $Y^1$ are the same or different and represent hydrogen, alkyl, halogen or alkoxy.

Z represents hydrogen, halogen, alkyl, alkoxy or aryloxy, $R_5$ represents hydrogen, alkyl, alkoxy or aryloxy $R_4$ represents alkyl or aryl, and $R_2$ and $R_3$ represent the same or different alkyl, aralkyl or aryl groups or one of $R_2$ and $R_3$ represents hydrogen and the other is alkyl, aralkyl or aryl, with the proviso that when Z or Y is alkoxy or aryloxy, $R_1$ is other than hydrogen.

The aryl groups in the above general formula particularly those at $R_1$, $R_2$, $R_3$ or $R_6$, may be substituted e.g. by halogen, alkyl having 1 to 20 carbon atoms, cycloalkyl having 3 to 12 carbon atoms, aralkyl having 7 to 12 carbon atoms, alkoxy having 1 to 20 carbon atoms or alkaryl groups having 7 to 22 carbon atoms or any combination thereof.

The compounds of formula (I) above exhibit markedly improved photochromic properties when compared with prior art compounds, and such improved properties enable the compounds to be used in many commercial applications.

As a consequence of further investigation of the nature of the compounds of formula (I) and the reversible photochemical cyclisation reaction which they undergo, I have discovered that further marked improvements in thermal stability and other desirable properties can be obtained by replacing the phenyl group containing the alkoxy or aryloxy group with a specific and narrowly defined series of heterocyclic groups.

SUMMARY OF THE INVENTION

In one of its broadest aspects the invention relates to a series of photochromic compounds having the following general formula (II):

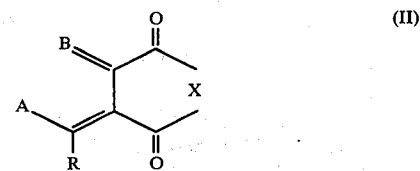

wherein X represents oxygen or $>NR_6$, $R_6$ being hydrogen, alkyl, aryl or aralkyl;

R represents an alkyl, aryl, aralkyl or heterocyclic group,

A represents a substituted or unsubstituted heterocyclic ring having one of the following structures:

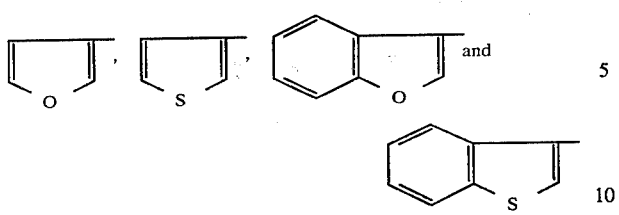

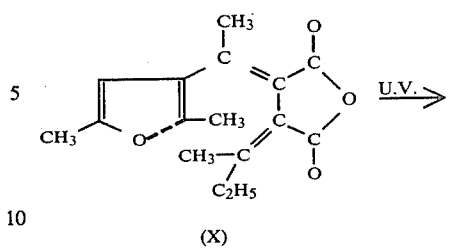

and B represent an adamantylidene group or the grouping

in which $R_2$ and $R_3$ independently represent an alkyl, aryl, aralkyl or a heterocyclic group or one of $R_2$ and $R_3$ represents hydrogen and the other an alkyl, aryl, aralkyl or a heterocyclic group.

In order to appreciate more readily the significance and scope of the present invention it is convenient to consider in turn certain sub-classes of compounds falling within the general formula (II).

Thus according to one aspect the present invention relates to compounds of the general formulae (III) and (IV) below:

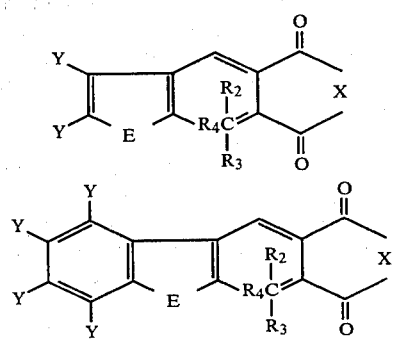

wherein
R, $R_2$, $R_3$ and X have the same significance as in general formula (II) above,
E represents oxygen or sulfur,
$R_4$ represents hydrogen, or an alkyl, aryl or aralkyl group, and each Y is in independently selected from hydrogen, halogen, alkyl, aryl, aralkyl, alkoxy and aryloxy groups.

Preferably Y represents hydrogen and $R_4$ represents lower alkyl, aryl or aralkyl.

When compounds of the general formulae (III) and (IV) are exposed to activating radiation, usually in the ultra violet range, ring closure occurs between the carbon atom to which the $R_2$ and $R_3$ groups are attached and the 2-position of the furyl or thienyl ring. The photocyclisation reaction is illustrated by the following typical case:

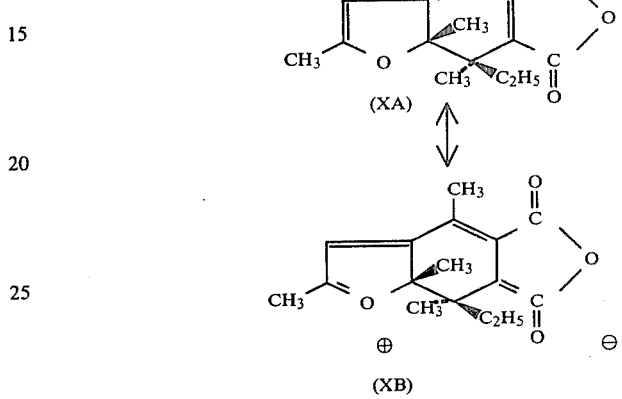

Under the influence of U.V. light the compound (X) is converted in high yield to the cyclic form (XA) which is resonance stabilised as shown in forms (XA) and (XB).

The cyclic form (for example structures (XA) and (XB)) is deeply coloured, usually exhibiting a visual effect in the bright red to deep purple range, and this is believed to arise from the extended conjugated double bond structure with the oxygen heteroatom at one end and the succinic anhydride carbonyl oxygen at the other. The resonance stabilisation of the coloured form is believed to be partly responsible for good thermal stability properties by inhibition of thermal side reactions such as a 1,5-hydrogenshift when $R_4$ is hydrogen.

In the case of compounds where $R_4$ is hydrogen, ring closure can also be induced in the dark by heating above 100° C. to give the coloured form which is stable at normal ambient temperatures but is reversed by white light. The optimum temperature is about 140° C., at which the ring closure reaction is fast relative to side reactions of the cyclic coloured form.

The presence of alkyl, aryl or aralkyl groups in the $R_2$, $R_3$ and $R_4$ position is preferred since a 1,5-hydrogen shift cannot then occur and thermally-induced disrotatory ring opening is prevented by steric interactions between the $R_4$ and the $R_2$ and $R_3$ groups.

The importance of selecting compounds in which the succinic anhydride or succinimide-residue is attached to the 3-position of a furyl or thienyl radical is demonstrated when, for example, one examines the properties of a 2-furfurylidene-succinic anhydride compound. Such compounds lack significant photochromic properties and it is thought that this is because: (a) while ring closure is theoretically possible, it would have to occur at the less reactive 3-position and (b) on ring closure, the heterooxygen is not in the terminal position of the coloured form so that the chromophore is shortened.

Attainment of photochromic properties also appears to be dependent on the introduction of a group other than hydrogen at R. Experiments have indicated that if R in formula (III) or (IV) is hydrogen, a photochemical cis-trans isomerisation is the predominant reaction when such compounds are exposed to activating radiation. Certainly in the case of such compounds where E is sulfur the photochromic properties are weak and when E is oxygen photochromic properties were not observed.

While the importance of the structural characteristics referred to above in the development of compounds having the desired photochromic properties must be stressed, the substituents in the heterocyclic ring have little or no influence on the basic character of the compounds and can be varied widely. Also the particular identity of the groups represented by R, $R_2$, $R_3$ and $R_4$ can be varied widely within the parameters indicated.

According to a further aspect, the invention relates to compounds of the general formula (V) and (VI) below:

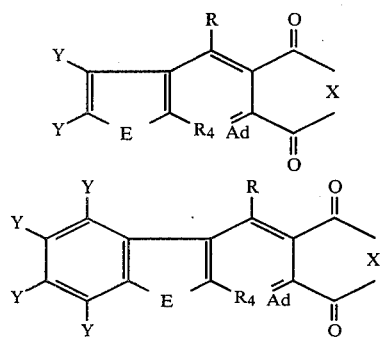

wherein R, $R_4$, X, E and Y have the same significance as in relation to formulae (III) and (IV) and Ad is an adamantylidene group.

On activation with U.V. light the compounds of formulae (V) and (VI) behave in a very similar manner to the compounds of formulae (III) and (IV), the adamantylidene group simply replacing the group $R_2$ and $R_3$. Compounds of formulae (V) and (VI) exhibit improved photosensitivity as compared with the compounds discussed above. They also show good thermal stability and the ability to undergo a large number of colour change cycles without substantial deterioration in the character of the absorption spectra as a result of formation of so-called fatique products of irreversible side reactions.

It is believed that the marked improvements in these desirable photochromic properties arises from the stable character of the adamantane ring, which possesses a structure virtually free from both angle and conformational strain and in which bond migration does not occur.

PREPARATION OF THE PHOTOCHROMIC COMPOUNDS

The Stobbe condensation provides a general procedure applicable to the preparation of the photochromic compounds of the present invention. A fairly comprehensive account of the Stobbe condensation and its application to the synthesis of a wide variety of succinic acid derivatives can be found in Chapter 1 of volume 6 of "Organic Reactions" published by Wiley, New York, 1951, pages 1 to 73.

For example compounds of formula (III) can be prepared by condensing a ketone of the formula:

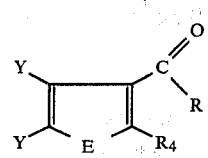

with an ester of a succinic acid ester of the formula:

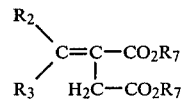

wherein R, $R_2$, $R_3$; $R_4$ and Y are as defined in relation to formula (III) and $R_7$ is the residue of an alcohol, by a Stobbe condensation, hydrolysing the half ester so produced to form the di-acid and then heating the resulting di-acid with an acid chloride to yield a product of formula (III) in which X is oxygen.

The Stobbe condensation is carried out by refluxing the reactants in t-butanol containing potassium t-butoxide if rigorous reaction conditions are required, or with sodium hydride in anhydrous toluene or ether if mild reaction conditions are needed. The product of this stage of the reaction is the half ester, i.e. where one $R_7$ group is hydrogen. This half ester is then converted into the di-acid by hydrolysis, e.g. by boiling with aqueous potassium hydroxide solution. The di-acid is then converted into its anhydride by a dehydration reaction comprising treating with an acid chloride. Preferably acetyl chloride is used.

Compounds of formula (III) produced in this way in which X is oxygen can be converted into the corresponding succinimide derivatives (where X is $>NR_6$) by heating equimolar proportions of the anhydride and the primary amine $R_6NH_2$ to produce the corresponding half amide. The half amide is then converted into the desired end product by heating with an acid chloride or acid anhydride, such as acetyl chloride or acetic anhydride. Reaction with the amine may be carried out in an organic solvent, e.g. benzene or chloroform.

An alternative method of preparing succinimide derivatives of formula III is to react the half ester product of the Stobbe condensation with a compound of the formula:

$R_6NHM_gBr$ to produce the corresponding succinamic acid, i.e. wherein the group $-COOR_7$ becomes $-CONHR_6$. This is then dehydrated by reaction with an acid chloride such as acetyl chloride.

Compounds of formula (IV) can be prepared in an analogous fashion using as starting material a ketone of formula:

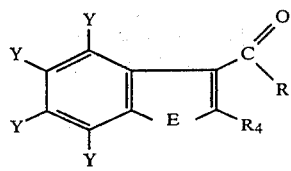

5

It will be appreciated from the above and from the cited chapter from "Organic Reactions" that the Stobbe condensation is a procedure of general application for the synthesis of fulgides in accordance with the invention as well as starting materials of formula:

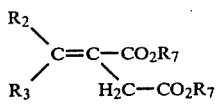

Fulgimides in which $R_6$ is hydrogen may be prepared by reacting the appropriate succinic anhydride with concentrated ammonia to produce the corresponding half amide acid and then reacting the product with diazomethane to yield the methyl ester of the half amide, followed by cyclisation using sodium ethoxide. This procedure is fully described in the paper by Goldschmidt et al, published in Leibigs Annalen der Chemie, 1957, volume 604, pages 121 to 132.

Compounds of formulae (V) and (VI) can be prepared in an analogous fashion to that described above using Adamantan-2-one as a starting material. Preparation of Adamantan-2-one is described in U.S. Pat. No. 3,257,456 and by Geluk et al, Organic Synthesis, 1973, volume 53, page 8.

The structure of Adamantan-2-one is shown below (formula 5). Adamantane, the root hydrocarbon (formula 3) can be prepared by hydrogenation of dicyclopentadiene (1) to endo-tetrahydro-dicyclopentadiene (2) followed by rearrangement of the latter using a catalyst comprising anhydrous aluminium chloride and hydrogen chloride (Schleyer et al. Organic Synthesis, 1962, volume 42, page 8).

Adamantanone (5) is obtained either by direct oxidation of adamantane or by a two stage process involving free radical hydroxylation of adamantane using peracetic acid and U.V. radiation to adamantan-2-ol (4) and oxidation of the product using a chromic acid/sulfuric acid mixture to adamantan-2-one (Schleyer et al JACS 1961, 83, p.182).

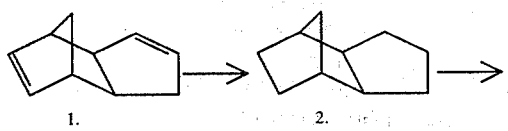

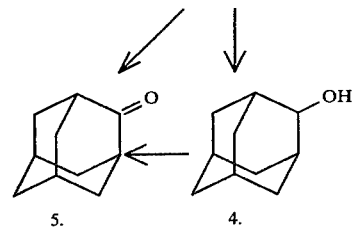

Photochromic compounds of formula (V) and (VI) can be prepared by refluxing adamantanone (5) with a succinate diester in a solution of potassium t-butoxide in t-butanol to give the potassium salt of the corresponding half ester. Boiling in a benzene/ethanol mixture containing concentrated hydrochloric acid yields an adamant-2-ylidene-succinate diester. These diesters are novel intermediates and have the following structure (formula 6):

![formula 6]

wherein Et is a residue of an alcohol.

Compounds of formula (V) or (VI) are obtained by reacting a diester of formula (6) with an appropriate ketone in the presence of sodium hydride. For example, by selecting a ketone of the formula ![ketones]

photochromic compounds are obtained having the formulae (7):

![formula 7]

wherein Ar = a, ![furan a]  b; ![furan b]

The corresponding succinimides (fulgimides) are prepared from the appropriate fulgides using the same techniques as described above in relation to compounds of formula (III) and (IV).

Reversible photocyclisation takes place when compounds of the formula (V) and (VI) are exposed to activating radiation, normally in the near ultraviolet range, e.g. about 330–400 nm. The coloured forms frequently possess a deep red colour and the reversion to the original form can normally be achieved by exposure to white light.

It is believed that the photocyclisation reaction involves formation of a linkage between the $\alpha$-carbon atom of the adamantane ring and the 2 position of the furyl or thienyl ring and migration of the double bonds in the resulting ring system to form a chain of conjugated double bonds extending from a carbonyl oxygen atom of the succinic anhydride residue to a heteroatom in the furyl or thienyl ring.

As indicated above, the nature of the radicals Y, $R_4$ and R in formulae III, IV, V and VI is not critical and can be varied widely without loss of the photochromic properties. Similarly the identity of the radicals $R_2$ and $R_3$ is not critical provided that both of $R_2$ and $R_3$ are not hydrogen.

Specific examples of groups which may be present in the photochromic compounds of the invention are as follows:

R, $R_2$ and $R_3$ radicals

May be selected from:
(i) alkyl groups containing from 1 to 20 carbon atoms, preferably 1 to 6 carbon atoms, e.g. methyl, ethyl, n-propyl, iso-propyl and butyl.
(ii) aryl groups containing from 6 to 14 carbon atoms, e.g. phenyl and naphthyl. The aryl groups may contain one or more substituents e.g. halogen, alkyl containing 1 to 20 carbon atoms, cycloalkyl containing 3 to 12 carbon atoms, aralkyl having 7 to 12 carbon atoms, alkoxy having 1 to 20 carbon atoms, e.g. methoxy, ethoxy, propoxy and bentoxy group and alkaryl groups having 7 to 22 carbon atoms.
(iii) a heterocyclic group such as 3-furyl or 3-thienyl which may be substituted with groups such as those listed below for $R_4$ and Y in the 2-and 4,5 positions respectively.

$R_4$ and Y radicals

May be selected from:
(i) hydrogen
(ii) halogen
(iii) alkyl having 1 to 20 carbon atoms
(iv) aryl having 6 to 14 carbon atoms, e.g. phenyl or naphthyl, which may be substituted as indicated above.
(v) aralkyl having 7 to 12 carbon atoms.

$R_6$ radical $R_6$ may be any of the $R_4$ or Y radicals except halogen.

Examples of alkyl groups which may be present as any of radical R, $R_2$, $R_3$, $R_4$, $R_6$ or Y are methyl, ethyl, n-propyl, iso-propyl, n-butyl, iso-butyl, sec-butyl, t-butyl, sec-amyl, t-amyl, n-hexyl, n-heptyl, t-octyl, nonyl, n-decyl, n-undecyl, n-dodecyl, n-pentadecyl, n-hexadecyl, and n-octadecyl.

Substituted aryl groups which may be represented by any of the above radicals include, methoxy phenyl dimethoxy phenyl, and piperonyl.

Suitable alkoxy groups include methoxy, ethoxy, propoxy and butoxy.

Preferred cycloalkyl groups are cyclopentyl and cyclohexyl.

Aralkyl groups which may be present as one of the above radicals include benzyl, $\alpha$-methyl-benzyl and $\alpha,\alpha$,-dimethyl benzyl.

Specific examples of alkaryl groups include methylphenyl, ethyl phenyl, iso-propyl phenyl, t-butyl phenyl, sec-butyl phenyl, amyl phenyl, n-dodecylphenyl and 2,4-dimethyl phenyl.

The improved photochromic properties of the compounds in accordance with the invention makes them suitable for a wide variety of practical applications as photochromic compositions or devices. The commercial applications of the compounds fall into two broad classes (1) those in which a temporary image is formed and (2) those in which use is made of the reduced transmission or reflection of light by the coloured forms.

In the first group of applications the photochromic compounds can be used with advantage in various reproduction, copying and information display systems. Specific examples are as follows:

Photography and Reproduction systems

Films or plates may be prepared by coating a support with a solution, dispersion or emulsion containing a compound or misture of compounds in accordance with the invention. The resulting films or plates can be used as temporary positives or negatives without any need for development or fixing from which permanent prints can be made using conventional photographic materials. The image can be erased and the same photochromic film or plate re-used repeatedly.

Reproduction and copying using plates or films are of particular value in making temporary copies e.g. from microfiche or to prepare a temporary master.

Photochromic display systems

Photochromic screens can also be used as information boards, e.g. at railway stations or airports or in special display systems such as flight simulators. The information can be written on the boards with a scanning laser or other light beam device and subsequently erased or updated.

The formation of the coloured cyclic structure is stimulated most effectively by exposure of the compounds to light in the near ultra-violet range, e.g. at about 330–400 mm. On removal of the activating radiation and in the presence of visible light, the compounds will revert to the non-coloured or less colour form but at normal ambient temperatures the change is very slow. The rate will depend upon the temperature (the higher the temperature, the greater the rate of reversion) and the nature of the substitutents. For example, the presence of alkyl or aryl groups at both $R_2$ and $R_3$ will effectively increase the half-life of the coloured form to infinity. For most of the applications described above it will be necessary or desirable to remove the image at a faster rate than the natural fading rate and this is readily achieved by exposure to a coherein light in the visible spectrum, preferably green light in the range of about 514–550 mm, which can be obtained using an argon ion laser. The second group of applications make use of the reduced light transmission properties of the coloured forms of the compounds. Thus photochromic packaging film (e.g. coated cellophane) can be used as an outer wrapper to protect products from the effects of sunlight, while allowing the products to be viewed through the wrapping in artificial light. Perishable foodstuffs and pharmaceuticals are examples of products which may be advantageously protect in this way.

Similarly shop windows or storage cabinets may be treated with the compounds of the invention so as to protect their contents. Paints can be formulated with the photochromic compounds so as to reduce the penetration of sunlight, thereby reducing dazzle, extending the life of the paint film or providing camouflage for the military.

Because many of the compounds of the present invention exhibit a high conversion into the coloured form, possess a high degree of thermal stability and negligible photochemical fatique, the compounds are well suited for use as chemical light meters. Thus they can be used to indicate a minimum light intensity or to detect U.V. light. Continuous monitoring of U.V. radiation flux enables assessment of atmospheric pollution levels and monitoring of U.V. radiation in sunlight is of value in the current endeavours to utilize solar energy directly.

For the above uses, the photochromic compounds are normally dispersed in a light transmissive vehicle to form a solution, emulsion or dispersion and then applied as a coating to a support, after which the continuous phase is removed. Alternatively the compounds may be incorporated within or impregnated into a support, which may be a plate, film, fabric, paper or sheet. Further alternative presentations are as a solid polycrystallite coating, as a large single crystal or as a fluid solution in a cell.

The invention will be illustrated by the following non-limiting Examples in which parts and percentages are by weight unless otherwise stated:

EXAMPLE 1

Preparation of (E)- and (Z)-α-2,5-dimethyl-3-furylethylidene (isopropylidene) succinic anhydrides.

3-Acetyl-2,5-dimethylfuran (7 parts) and diethyl isopropylidenesuccinate (10 parts) were added to a suspension of sodium hydride (5 parts) in benzene (100 parts by volume). When reaction was complete, a small amount of ethanol was added to destroy excess sodium hydride, the solvent was removed and the residue acidified with hydrochloric acid. The liberated half esters (8 parts) were hydrolysed with 10% ethanolic potassium hydroxide and the diacids precipitated by addition of hydrochloric acid. The dried acids (1 part) with acetyl chloride (50 parts by volume) was allowed to stand at room temperature until all the acid had dissolved. The solvent was removed and the (E)- and (Z)- isomers separated by fractional crystallisation from chloroform and petrol giving pale yellow crystals m.p. 126°–127° and 158°–159° respectively, which on irradiation at 366 nm. turn purple. The colour is reversed on exposure to white light.

EXAMPLE 2

Example 1 was repeated, using 2-benzyl-3-acetylbenzofuran as reactant, in place of 3-acetyl-2,5-dimethylfuran. (Z)-α-2-benzyl-3-benzofurylethylidene (isopropylidene) succinic anhydride was obtained as pale yellow needles, m.p. 178°–180° (from petrol) which on irradiation at 366 nm. turn red. The colour is reversed by white light.

EXAMPLE 3

Example 1 was repeated, using 3-acetyl-2,5-dimethylthophene as reactant, in place of 3-acetyl-2,5-dimethylfuran. (Z)-α-2,5-dimethyl-3-thienylethylidene (isopropylidene) succinic anhydride was obtained nearly colourless crystals, m.p. 155°–156° which on irradiation at 366 nm. turn deep red. The colour is reversed by white light.

EXAMPLE 4

Example 1 was repeated, using diethyl (E)-piperonylidenesuccinate as reactant, in place of diethyl isopropylidenesuccinate. The dried diacid (1 part) with acetic anhydride (15 parts by volume) was allowed to stand at room temperature for about half an hour. (Z)-α-2,5-dimethyl-3-furylethylidene-(E)-piperonylidenesuccinic anhydride was obtained as orange-yellow crystals m.p. 134°–135° (from chloroform/petrol) which on irradiation at 366 nm turn red. The colour is reversed by white light.

EXAMPLE 5

Example 4 was repeated, using 3-acetyl-2,5-dimethylthiophene as reactant, in place of 3-acetyl-2,5-dimethylfuran. (Z)-α-2,5-dimethyl-3-thienylethylidene-(E)-piperonylidenesuccinic anhydride was obtained as pale yellow crystals, m.p. 149°–150° (from chloroform/petrol), which on irradiation at 366 nm turn red. The colour is reversed by white light.

EXAMPLE 6

Example 1 was repeated, using 3-acetyl-2-methylfuran as reactant, in place of 3-acetyl-2,5-dimethylfuran. (E)-α-2-Methyl-3-furylethylidene-(isopropylidene) succinic anhydride was obtained as pale yellow needles, m.p. 102°–103° (from petrol) which on irradiation at 366 nm. turn red. The colour is reversed by white light.

EXAMPLE 7

Preparation of (Z)-α-2,5-diphenyl-3-furylethylidene (isopropylidene)-succinic anhydride.

3-Acetyl-2,5-diphenylfuran (1 part) and diethyl isopropylidene-succinate (1 part) were added to potassium t-butoxide (1 part) in t-butanol (20 parts by volume). When reaction was complete, the procedure described in example 1 was used. The (Z)-anhydride was obtained as pale yellow crystals, m.p. 150° (from ethanol), which on irradiation at 366 nm turn reddish-blue. The colour is reversed by white light.

EXAMPLE 8

Example 1 was repeated, using diethyl diphenylmethyl enesuccinate as reactant, in place of diethyl isopropylidenesuccinate. (Z)-α-2,5-Dimethyl-3-furylethylidene(diphenylmethylene)succinic anhydride was obtained as light red needles, m.p. 188°–190° (from ethanol) which on irradiation at 366 nm turn deep red. The colour is reversed by white light.

EXAMPLE 9

Example 1 was repeated, using diethyl 2-butenylidene succinate as reactant, in place of diethyl isopropylidenesuccinate. (E)-α-2,5-Dimethyl-3-furylethylidene-(Z)-2-butenylidene succinic anhydride was obtained as colourless cubes, m.p. 96°–97° (from petrol) which on irradiation at 366 nm turn red. The colour is reversed by white light.

EXAMPLE 10

(Z)-α-2,5-Dimethyl-3-furylethylidene (isopropylidene) succinic anhydride (1 part), as described in example 1, in toluene (30 parts by volume) and p-anisidine (1 part) were heated for 48 hours at 110°. Solvent was removed and the residual succinamic acids dissolved in acetyl chloride (10 parts by volume) and allowed to stand at room temperature for 1 hour. The solvent was removed and the (E)-α-2,5-dimethyl-3-furyle-thylidene(isopropylidene)-N-pmethoxyphenylsuccinimide crystallised from ethanol, giving pale yellow prisms, m.p. 175°–176° which on exposure to daylight or 366 nm radiation turn red. The colour is reversed by white light.

EXAMPLE 11

(Z)-α-2,5-Dimethyl-3-thienylethylidene(isopropylidene) succinic anhydride (5 parts), as described in example 3, in toluene (150 parts) and aniline (2 parts) were heated for 24 hours at 110°. Petrol was added and the precipitated succinamic acids separated. The dry acids (1 part) were dissolved in a 1:1 mixture of acetyl chloride and ether (100 parts by volume) and left to stand at room temperature for 1 hour. Solvent was removed and the residue was crystallised from ether and petrol, giving (Z)-α-2,5-dimethyl-3-thienylethylidene (isopropylidene)-N-phenyl succinimide, near colourless needles, m.p. 131°–133°, which turn purple on irradiation at 366 nm. The colour is reversed by white light.

EXAMPLE 12

Preparation of 2,5-dimethyl-3-furyl(3',5'-dimethyoxyphenyl) methylene-E-benzylidenesuccinic anhydride. 3-(3',5'-Dimethoxybenzoyl)-2,5-dimethylfuran (10 parts) and diethyl (E)-benzylidenesuccinate (10 parts) were added to a suspension of sodium hydride (3 parts) in toluene (150 parts by volume). Work up as described in example 1 gave the half ester which was hydrolysed with 10% ethanolic potassium hydroxide, and the diacid precipitated by addition of hydro-chloric acid. The dried diacid was treated with acetyl chloride as before. The solvent was removed and the anhydride was crystallised from benzene and petrol giving red crystals, m.p. 208°–210° which turn deeper red on irradiation at 366 nm. The colour is reversed on exposure to white light.

EXAMPLE 13

(1) Preparation of diethyl adamant-2-ylidenesuccinate (9)

Adamantan-2-one (50 parts) and diethyl succinate (58 parts) in t-butanol (200 parts by volume) were added to a solution of potassium t-butoxide in t-butanol (prepared by dissolving potassium (13.5 parts) in t-butanol (700 parts by volume). The reaction mixture was boiled (2½ h), cooled and the solid filtered off and extracted with ether. The ether extracted gave adamantanone (20 parts). The ether-insoluble solid, the potassium salt of the itaconic half ester, was dissolved in water and acidified with 5 M hydrochloric acid, giving ethyl adamant-2-ylidenesuccinate (50 parts), m.p. 85°–87° C., 82% yield based on adamant-2-one consumed. The half ester was boiled with ethanol (75 parts by volume), benzene (225 parts by volume) and conc. hydrochloric acid (2 parts by volume) and the water azeotroped off using a Dean and Stark apparatus. Unchanged half ester was extracted with sodium carbonate solution, the organic layer was dried (magnesium sulphate), filtered and the solvent removed. The diester was obtained as a colourless oil (47 parts) 86% yield.

(ii) Preparation of adamant-2-ylidene (2'-methyl-3'-furyl) ethylidene succinic anhydride (10a)

2-Methyl-3-acetylfuran (11 parts) and diethyl adamant-2-ylidene succinate (27 parts) in toluene (100 parts by volume) was added slowly to a stirred suspension of sodium hydride (50% dispersion in oil) (9 parts) in toluene (100 parts by volume). The reaction mixture was stirred (1 h) until evolution of hydrogen had ceased and then the temperature of the reaction mixture was raised to 30° C. and stirred for a further hour. The reaction mixture was cooled, poured onto crushed ice, and the toluene layer separated, extracted with 2 M sodium hydroxide and the alkaline extracts combined. The latter was acidified with conc.hydrochloric acid and the liberated oil extracted with toluene, dried and solvent removed. The residual oil was boiled (1 h) with potassium hydroxide (15 parts) in 2-propanol (200 parts by volume). The solution was cooled and the dipotassium salt filtered off, dissolved in water, and acidified with conc.hydrochloric acid. The diacid which separated was extracted into ether, dried (magnesium sulphate) and ether removed. The diacid was boiled (1 h) with acetyl chloride (175 parts by volume) and the acetyl chloride removed. The residual oil was triturated with ether and the resulting solid, Soxhlet extracted with petroleum b.p. 60°–80° C. Removal of the petrol left a solid which was crystallised from 1:3 mixture by volume of chloroform and petroleum b.p. 60°–80° C., giving the anhydride in nearly colourless crystals, m.p. 197°–198.5° C., which turn deep red on irradiation at 366 nm. The colour is reversed by white light.

EXAMPLE 14

Preparation of adamant-2-ylidene-(2',5'dimethyl-3'-furyl) ethylidenesuccinic anhydride (10b)

The procedure described in part (ii) of Example 1 was repeated using 2,5-dimethyl-3-acetylfuran (7 parts) and diethyl adamant-2-ylidenesuccinate (15 parts) in toluene and sodium hydride (50% dispersion in oil) (5.3 parts) in toluene. The anhydride separated from ether and was crystallised from petroleum 60°–80° C., giving colourless needles, m.p. 177°–179° C., which turn dark red on irradiation at 366 nm. The colour is reversed by white light.

The following Examples are given to illustrate the production of photochromic films and screens in accordance with the invention.

EXAMPLE 15

10 grams of the pale yellow crystals obtained in Example 3 were dissolved, together with 100 grams of cellulose acetate, in 1 liter of a 50/50 volume mixture of 2-hydroxy ethyl acetate and acetone. The resulting solution was filtered and coated onto a cellulose acetate base sheet using a blade over roller coating technique to achieve a wet coating thickness of 120 microns. After drying at 120° C., the coating had a dry thickness of about 12 microns. The resulting screen produced a deep red image when exposed to a light beam having a wavelength of 366 nm, the image being extinguished by subsequent exposure to a light beam at 550 nm and could be used as a display screen. Screens of higher optical quality can be produced using glass plates in place of cellulose acetate film.

EXAMPLE 16

A solution containing 10 grams of the crystals obtained in Example 1 were dissolved in 1 liter of toluene with warming. A piece of "Wratten" 50 grade paper was dipped into the solution, removed and dried in air at room temperature. A red image was obtained by exposing the impregnated paper to light of wavelength 366 nm and, the impregnated paper was suitable for making temporary copies, e.g. from microfiche, under normal ambient temperatures.

I claim:

1. A photochromic compound of the general formula:

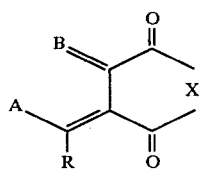 (II)

wherein

X represents oxygen or $\geq NR_6$, $R_6$ being hydrogen or an alkyl, aryl or aralkyl group;

R represents an alkyl or aryl group;

A represents a 3-furyl, 3-thienyl, 3-benzofuryl or 3-benzothienyl group; and

B represents an adamantylidene group or the grouping

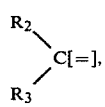

in which $R_2$ and $R_3$ independently represent an alkyl, aryl, or a heterocyclic group containing a furyl or thienyl ring or one of $R_2$ and $R_3$ represents hydrogen and the other represents an alkyl or aryl group.

2. The compound of claim 1, wherein R represents a lower alkyl, phenyl or naphthyl group.

3. The compound of claim 2, wherein the phenyl or naphthyl group is substituted with one or more substituent groups selected from the group consisting of alkyl, cycloalkyl, alkoxy and alkaryl groups.

4. The compound of claim 2, wherein at least one of $R_2$ and $R_3$ is alkyl or aryl.

5. A photochromic compound having the general formula:

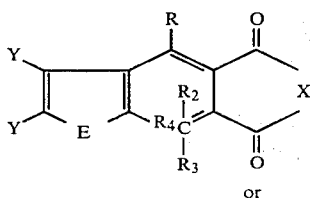 (III)

or

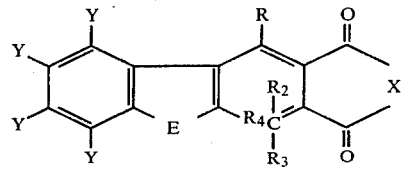 (IV)

wherein X represents oxygen or $>NR_6$, $R_6$ being hydrogen or an alkyl, cycloalkyl, aryl or aralkyl group;

R represents an alkyl or aryl group;

$R_2$ and $R_3$ independently represent an alkyl or aryl group or one of $R_2$ and $R_3$ represents hydrogen and the other represents an alkyl or aryl group;

E represents oxygen or sulphur;

$R_4$ represents hydrogen or an alkyl, aryl or aralkyl group; and each Y is independently selected from hydrogen, halogen, alkyl, aryl, or aralkyl groups.

6. A compound as claimed in claim 5, wherein at least one of $R_2$ and $R_3$ is alkyl or aryl.

7. A compound as claimed in claim 5, wherein one or more of the groups $R_6$, R, $R_2$, $R_3$, and $R_4$ is an alkyl group containing 1 to 18 carbon atoms.

8. A compound as claimed in claim 7, wherein said alkyl group is a lower alkyl group containing 1 to 6 carbon atoms.

9. A compound as claimed in claim 5, wherein X represents oxygen or $>NR_6$, $R_6$ being hydrogen, lower alkyl, phenyl or benzyl;

R represents lower alkyl or phenyl, Y represents hydrogen, lower alkyl or phenyl and $R_4$ represents hydrogen, lower alkyl, phenyl or benzyl;

$R_2$ and $R_3$ are the same or different and one represents hydrogen and the other lower alkyl or phenyl or both represent lower alkyl or phenyl.

10. A compound as claimed in claim 9, wherein one or more of the phenyl groups represented by R, $R_2$, $R_3$, $R_4$ or Y are substituted with one or more ring substituents.

11. A compound as claimed in claim 10, wherein the substituents are lower alkoxy or the group

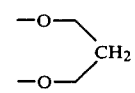

12. A photochromic compound having the general formula:

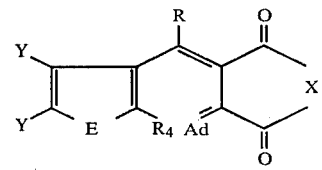 (V)

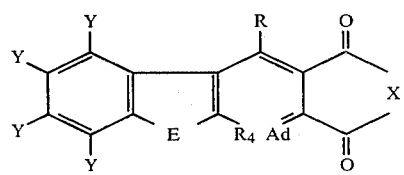 (VI)

wherein X represents oxygen or $>NR_6$, $R_6$ being hydrogen or an alkyl, aryl or aralkyl group;

R represents an alkyl, aryl or aralkyl group;

E represents oxygen or sulphur;

$R_4$ represents hydrogen or an alkyl, aryl or aralkyl groups;

each Y is independently selected from hydrogen, halogen, alkyl, aryl, aralkyl, alkoxy, and aryloxy groups and $R_2$ and $R_3$ independently represent an alkyl aryl or aralkyl group or one of $R_2$ and $R_3$ represents hydrogen and the other represents an alkyl, aryl or aralkyl group.

13. A method of forming a temporary image on a surface using activating radiation which comprises the steps of:
(a) forming a photochromic surface comprising a photochromic compound having the general formula (II) below and a support therefor,

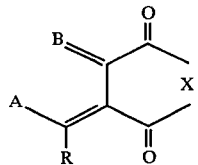
(II)

wherein X represents oxygen or $>NR_6$, $R_6$ being hydrogen or an alkyl, aryl, or aralkyl group;

R represents an alkyl or aryl group;

A represents a 3-furyl, 3-thienyl, 3-benzofuryl or 3-benzothienyl group;

B represents an adamantylidene group or the grouping

in which $R_2$ and $R_3$ independently represent an alkyl, aryl, or a heterocyclic group containing a furyl or thienyl ring or one of $R_2$ and $R_3$ represents hydrogen and the other represents an alkyl or aryl group, and (b) irradiating the photochromic surface through an image forming means whereby areas of the surface exposed to the radiation exhibit a change of colour resulting from reversible photocyclisation of the photochromic compound.

14. The method of claim 13, wherein the activating radiation is U.V. light.

15. The method of claim 13, wherein the photochromic surface comprises a matrix which is capable of transmitting light having said photochromic compound dispersed therein.

16. A compound as claimed in claim 1, wherein the compound is 2,5-dimethyl-3-furyl(3',5'-dimethoxyphenyl) methylene-E-benzylidenesuccinic anhydride.

17. A photochromic compound having the general formula:

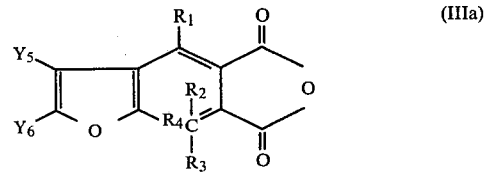
(IIIa)

or

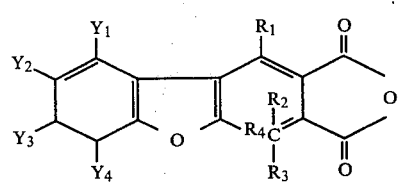
(IVa)

wherein:
$R_1$, $R_2$, and $R_3$, may be the same or different, and represent alkyl or aryl;

$R_4$ represents hydrogen, alkyl, aryl, or aralkyl; and $Y_1$, $Y_2$, $Y_3$, $Y_4$, $Y_5$, and $Y_6$, may be the same or different, and represent hydrogen, halogen, alkyl, aryl, or aralkyl.

18. A photochromic device which comprises a photochromic compound as defined in claim 1 in the form of a coating on a light transparent support.

19. A photochromic device which comprises a photochromic compound as defined in claim 1 dispersed in a matrix which is transparent to light.

20. A compound as claimed in claim 1, wherein R, $R_2$ and $R_3$ or R and one of $R_2$ and $R_3$ represent aryl substituted with alkyl.

21. A compound as claimed in claim 5, wherein R, $R_2$ and $R_3$ or R and one of $R_2$ and $R_3$ represent aryl substituted with alkyl.

22. The method of claim 13, wherein R, $R_2$ and $R_3$ or R and one of $R_2$ and $R_3$ represent aryl substituted with alkyl.

23. The compound of claim 17, wherein $R_1$, $R_2$ and $R_3$ represent aryl substituted with alkyl.

24. The compound of claim 5, wherein Y is independently selected from alkyl or aryl and alkyl is alkoxy and aryl is aryloxy.

25. The compound of claim 17, wherein $Y_1$, $Y_2$, $Y_3$, $Y_4$, $Y_5$ and $Y_6$ may be the same or different, and represent alkyl or aryl and alkyl is alkoxy and aryl is aryloxy.

* * * * *

UNITED STATES PATENT AND TRADEMARK OFFICE
CERTIFICATE OF CORRECTION

PATENT NO. : 4,220,708  
DATED : September 2, 1980  
INVENTOR(S) : Harold George HELLER Page 1 of 4

It is certified that error appears in the above—identified patent and that said Letters Patent is hereby corrected as shown below:

Column 2, lines 5-10, formula (I) should appear as follows:

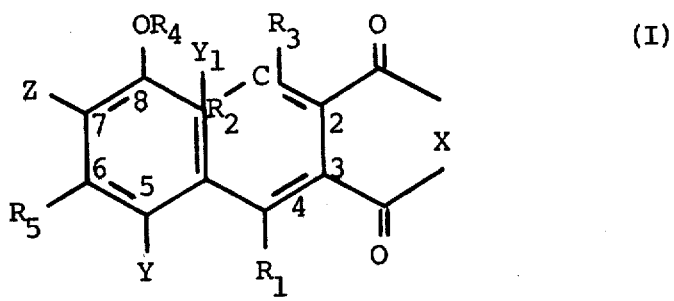

(I)

UNITED STATES PATENT AND TRADEMARK OFFICE
CERTIFICATE OF CORRECTION

PATENT NO. : 4,220,708  
DATED : September 2, 1980  
INVENTOR(S) : Harold George HELLER It is certified that error appears in the above—identified patent and that said Letters Patent is hereby corrected as shown below:

Column 4, lines 1-30, compounds (X), (XA) and (XB) should appear as follows:

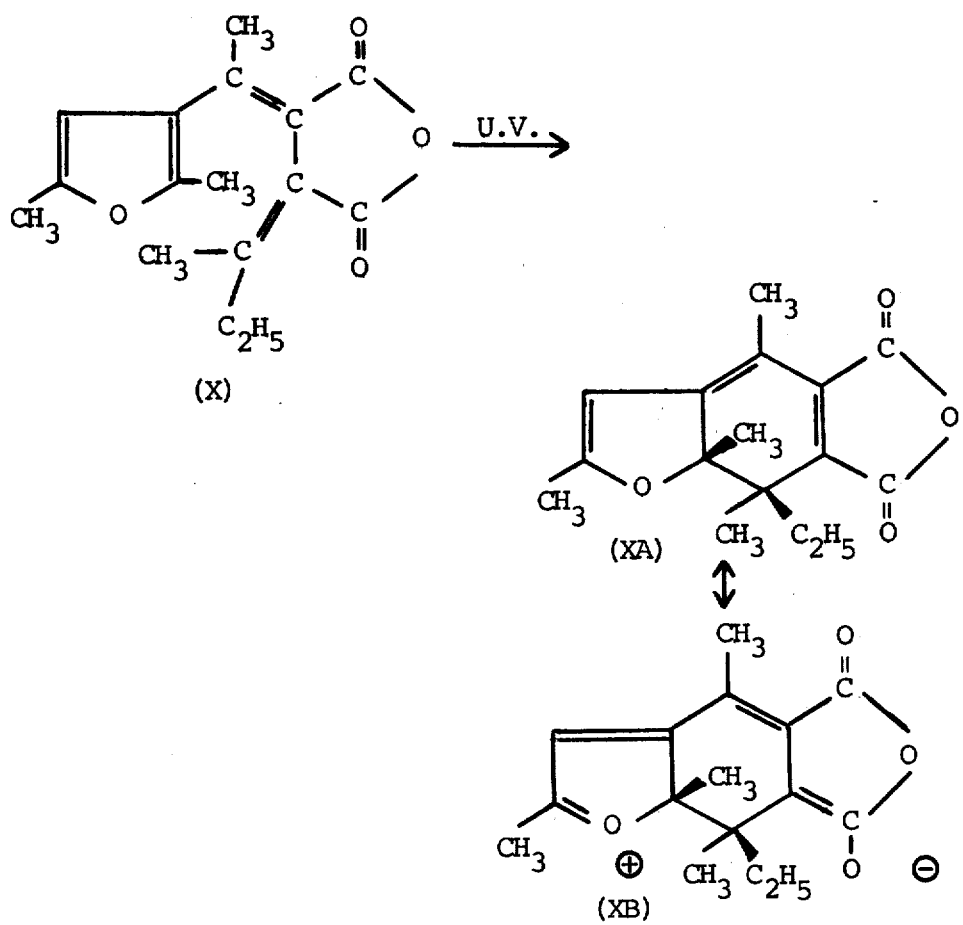

UNITED STATES PATENT AND TRADEMARK OFFICE
CERTIFICATE OF CORRECTION

PATENT NO. : 4,220,708
DATED : September 2, 1980
INVENTOR(S) : Harold George HELLER It is certified that error appears in the above—identified patent and that said Letters Patent is hereby corrected as shown below:

Claim 1, column 15, line 28, " $\geq NR_6$ " should read -- $> NR_6$ --; and lines 36-40, the formula should read:

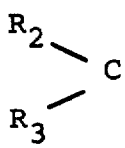

Claim 13, column 17, lines 36-40, the formula should read:

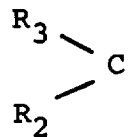

UNITED STATES PATENT AND TRADEMARK OFFICE
CERTIFICATE OF CORRECTION

PATENT NO. : 4,220,708

DATED : September 2, 1980

INVENTOR(S) : Harold George HELLER

It is certified that error appears in the above—identified patent and that said Letters Patent is hereby corrected as shown below:

Claim 17 (column 18, line 20), formula (IVa) should appear as follows:

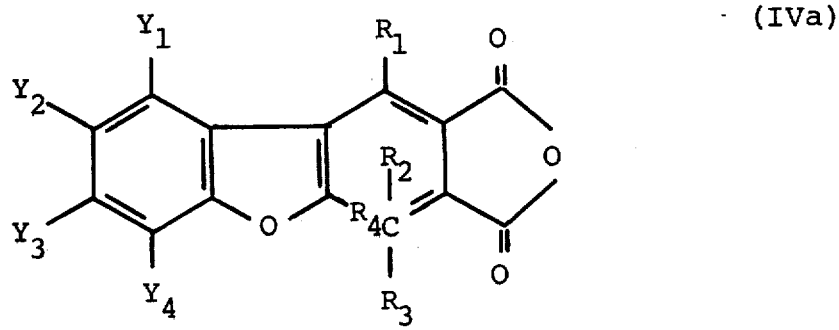

(IVa)

Signed and Sealed this

Second Day of February 1982

[SEAL]

Attest:

GERALD J. MOSSINGHOFF

Attesting Officer    Commissioner of Patents and Trademarks